United States Patent [19]

Schnur

[11] Patent Number: 4,457,939

[45] Date of Patent: Jul. 3, 1984

[54] ALDOSE REDUCTASE INHIBITING 5-(2-ALKOXY-3-SUBSTITUTED PHENYL)HYDANTOINS

[75] Inventor: Rodney C. Schnur, Noank, Conn.

[73] Assignee: Pfizer Inc., New York, N.Y.

[21] Appl. No.: 438,200

[22] Filed: Nov. 1, 1982

[51] Int. Cl.$^3$ ............................................ A61K 31/415
[52] U.S. Cl. ................................ 424/273 R; 548/314; 568/424; 568/442
[58] Field of Search ..................... 548/314; 424/273 R

[56] References Cited

FOREIGN PATENT DOCUMENTS 2012756 8/1979 United Kingdom ................ 548/314
2053206 2/1981 United Kingdom ................ 548/314

Primary Examiner—Richard A. Schwartz
Attorney, Agent, or Firm—Charles J. Knuth; A. E. Frost; Mark Dryer

[57] ABSTRACT

A series of 5-(2-alkoxy-3-substituted phenyl)hydantoins and pharmaceutically acceptable salts thereof useful as aldose reductase inhibitors and as therapeutic agents for the treatment of chronic diabetic complications; intermediates therefore; and processes for preparation of said compounds.

8 Claims, No Drawings

ALDOSE REDUCTASE INHIBITING 5-(2-ALKOXY-3-SUBSTITUTED PHENYL)HYDANTOINS

BACKGROUND OF THE INVENTION

This invention relates to novel 5-(2-alkoxy-3-substituted phenyl)hydantoins and to pharmaceutically acceptable salts thereof useful as inhibitors of aldose reductase and as therapeutic agents for the treatment of chronic diabetic complications.

Despite the widespread use of insulin and of the availability of a large number of synthetic hypoglycemic agents such as the sulfonylureas (e.g. chlorpropamide, tolbutamide, acetohexamide) and biguanides (e.g. phenformin), the search for improved hypoglycemic agents continues. More recently, efforts have been directed to controlling certain chronic complications of diabetes, such as diabetic cataracts, neuropathy and retinopathy. Such efforts have given rise to development of aldose reductase inhibitors, compounds which inhibit the activity of the enzyme aldose reductase which is primarily responsible for regulating reduction of aldoses to the corresponding polyols. In this way, unwanted accumulation of galactitol in the lens of galactosemic subjects and of sorbitol in the lens, kidney and peripheral nervous cord of various diabetic subjects is prevented or reduced. References which describe aldose reductase inhibitors are U.S. Pat. No. 3,821,383—1,3-dioxo-1H-benz[d,e]isoquinoline-2(3H)-acetic acid and related compounds; U.S. Pat. No. 4,200,642—spiro-oxazolidine-2,4-diones; U.S. Pat. Nos. 4,117,230; 4,130,714; 4,147,797; 4,210,756; 4,235,911 and 4,282,229, each of which describes certain spirohydantoins; and the concurrently filed application of Rizzi et al., entitled "5-(Substituted Phenyl)Hydantoins", and identified by the U.S. Ser. No. 438,199.

U.S. Pat. No. 4,281,009 describes a series of 5,5-disubstituted hydantoins in which one substituent is a substituted phenyl group and the other an alkyl or a heterocyclic group, said compounds being useful for treatment of diseases caused by stress.

Henze et al., J. Am. Chem. Soc. 64, 522-3 (1942) describe 5-phenylhydantoin and certain 5-(mono- and di-substituted phenyl)hydantoins wherein the substituents are hydroxy, alkoxy, formyl, methyl, chloro or dimethylamino. Other 5-(substituted phenyl)hydantoins are disclosed in U.S. Pat. No. 3,410,865 and in British patent application Ser. No. 2,063,206A. None of these known 5-(phenyl)hydantoins are reported to be aldose reductase inhibitors or to have a thio, sulfinyl or sulfonyl substituent in the phenyl ring.

SUMMARY OF THE INVENTION

It has now been found that certain 5-(2-alkoxy-3-substituted)phenyl hydantoins of formula I below and pharmaceutically acceptable salts thereof are useful as aldose reductase inhibitors and as therapeutic agents for the prevention and/or alleviation of chronic diabetic complications.

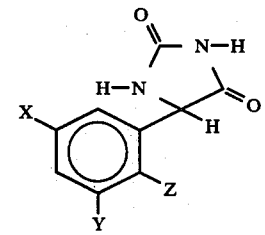

In formula (I),
X is chloro, fluoro, ($C_{1-4}$)alkyl, or nitro;
Y is chloro, fluoro or ($C_{1-4}$)alkyl; and
Z is ($C_{1-4}$)alkoxy.

The preferred compounds are those wherein X is fluoro or chloro; Y is fluoro, chloro or methyl, and Z is methoxy or ethoxy.

Because of the acidic hydrogen atom in the hydantoin ring of the compounds of formula I, salts can be formed with pharmaceutically acceptable cations by conventional methods. Thus, these salts may be readily prepared by treating the compound of formula I with an aqueous solution of the desired pharmaceutically acceptable cation and evaporating the resulting solution to dryness, preferably under reduced pressure. Alternatively, a lower alkyl alcohol solution of the compound of formula I may be mixed with an alkoxide of the desired metal and the solution subsequently evaporated to dryness. Suitable pharmaceutically acceptable cations for this purpose include, but are not limited to, potassium, sodium, ammonium, calcium and magnesium, aluminum, benzathine, piperazine, N-methylglucamine and procaine.

Also embraced by the present invention are pharmaceutical compositions comprising a pharmaceutically acceptable carrier and a compound of formula I in an amount effective for the treatment of diabetes-associated complications, including diabetic cataracts, neuropathy and retinopathy. Preferred compounds for use in such pharmaceutical compositions are those having the preferred substituents as defined herein above.

The present invention further includes a method of treatment of diabetes-associated complications, including diabetic cataracts, neuropathy and retinopathy, comprising administering to a subject in need of treatment an effective amount of a compound of formula I, preferably a compound having the preferred substituents for X, as defined herein above.

DETAILED DESCRIPTION OF THE INVENTION

The compounds of this invention are prepared via the sequence:

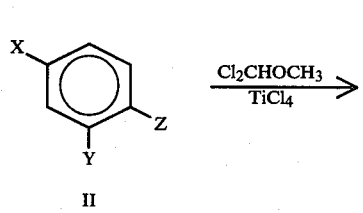

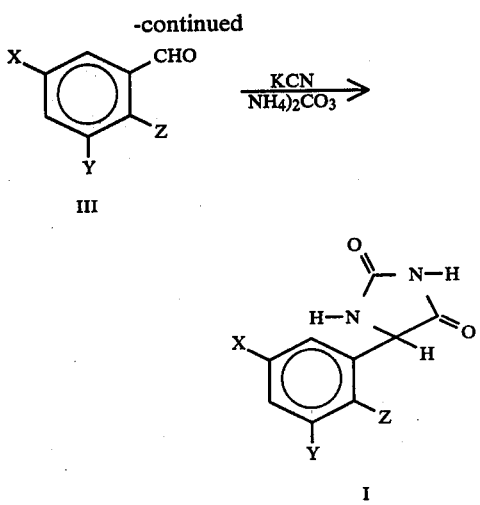

Convenient starting materials are the appropriate phenyl alkyl ethers of formula II or the 2-alkoxybenzaldehydes of formula III. Many of the required phenyl alkyl ethers or benzaldehyde derivatives are known compounds. Those that are not described in the literature are readily preparable by methods known to those skilled in the art.

In the first step of the sequence, the appropriate phenyl alkyl ether (formula II) is formylated to give the corresponding aldehyde derivatives by direct formylation of the benzene ring using alpha,alphadichloromethyl methyl ether and titanium tetrachloride. The reaction is conducted in a reaction-inert solvent such as a halo carbon, e.g. dichloromethane, chloroform, dichloroethane and carbon tetrachloride, and at a temperature of from about $-10°$ C. to $+30°$ C. In general, the compound to be formylated is added to a solution of the titanium tetrachloride reagent. An excess of reagent, up to 100% excess, is usually used to insure complete reduction. The formylating agent, dichloromethyl methyl ether is then added dropwise to this reaction mixture. The unreacted and/or excess reagents are destroyed by addition of a large excess of water. The reaction product is isolated by known procedures.

Alternatively, the required benzaldehyde reactants (III) are made from the appropriate phenol via the Duff reaction which comprises formylation of a phenol with hexamethylenetetramine in the presence of an acidic catalyst. The 2-hydroxy benzaldehyde derivative thus produced is then alkylated via the Williamson reaction to afford the desired 2-alkoxybenzaldehyde reactant (III).

A still further method for producing the necessary 2-hydroxybenzaldehyde reactants comprises reaction of the appropriate phenol compound; i.e., a 2-Y-4-X-disubstituted-hydroxy benzene, with chloroform in aqueous NaOH (Reimer-Tiemann reaction) to afford the desired 2-hydroxy-3-Y-5-X benzaldehyde, which is alkylated by the method described above.

The benzaldehyde derivative (III) is converted to the hydantoin (I) by reaction with ammonium carbonate and potassium (or sodium) cyanide in aqueous alcohol solution at a temperature of from 50°-60° C. for from 2 to 24 hours. Molar ratios of benzaldehyde reactant:potassium (or sodium) cyanide:ammonium carbonate of from 1:2:4 afford satisfactory yields of the desired hydantoin. The product is recovered by acidifying the reaction mixture and extracting it with a water-immiscible solvent such as ethyl acetate.

The novel compounds of formula I and the pharmaceutically acceptable salts thereof are useful as inhibitors of the enzyme aldose reductase in the treatment of chronic complications of diabetes, such as diabetic cataracts, retinopathy and neuropathy. As used in the claims and specification hereof, treatment is meant to include both the prevention or alleviation of such conditions. The compounds may be administered to a subject in need of treatment by a variety of conventional routes of administration, including oral, parenteral and topical. In general, these compounds will be administered orally or parenterally at dosages between about 0.25 and 25 mg/kg body weight of the subject to be treated per day, preferably from about 1.0 to 10 mg/kg. However, depending on the condition of the subject being treated, some variation in dosage will necessarily occur. The person responsible for administration will, in any event, determine the appropriate dose for the individual subject.

The novel compounds of this invention can be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate can be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type can also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, together with diluents such as water, ethanol, propylene glycol, glyercine and combinations thereof.

For parenteral administration, solutions of the novel compound of formula I in sesame or peanut oil, aqueous propylene glycol, or in sterile aqueous solution can be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The higher solubility of the present compounds of formula I and of the pharmaceutically acceptable salts thereof in aqueous solution, compared to other similar compounds, is advantageous not only for the preparation of aqueous pharmaceutical compositions for parenteral administration, as described above, but more particularly for the preparation of pharmaceutical compositions suitable for use as ophthalmic solutions. Such ophthalmic solutions are of principal interest for the treatment of diabetic cataracts by topical administration and the treatment of such conditions in this manner is a preferred embodiment of the present invention. Thus, for the treatment of diabetic cataracts the compounds of this invention are administered to the eye of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, PA). The ophthalmic preparation will contain a compound of formula I or a pharmaceutically acceptable salt thereof in a concentration from about 0.1 to about 5% by weight, preferably from about 0.5 to about 2% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potassium borate, sodium and potassium carbonate, sodium acetate, sodium biphosphate and the like, in amounts sufficient to maintain the pH at between about 6 and 8, preferably between about 7 and 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinvylpyrolidone, carboxymethylcellulose and the like. The ophthalmic preparation will be administered topically to the eye of the subject in need of treatment by conventional methods, for example in the form of drops or by bathing the eye in the ophthalmic solution.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized (i.e. diabetic) rats; (3) measuring their ability to reverse already elevated sorbitol levels in the sciatic nerve and lens of chronic streptozotocin-induced diabetic rats; (4) measuring their ability to prevent or inhibit galactitol formation in the lense of acutely galactosemic rats; and (5) measuring their ability to delay cataract formation and reduce the severity of lens opacities in chronic galactosemic rats. Suitable experimental procedures are described in U.S. Pat. No. 3,821,383 and the references cited therein.

In the examples which follow, no effort was made to optimize the yields of a given reaction. All nuclear magnetic resonance data (NMR) are in standard notation and are reported in parts per million (ppm) downfield from trimethylsilane. Deuterated dimethylsulfoxide (DMSO-$d_6$) was used as solvent in all examples.

EXAMPLE 1

5-(5-Chloro-2-methoxy-3-methylphenyl)hydantoins

A mixture of 5-chloro-2-methoxy-3-methylbenzaldehyde (1.22 g, 0.0066 mol), potassium cyanide (0.86 g, 0.014 mol), ammonium carbonate (2.53 g, 0.0264 mol) and 50% aqueous ethanol (150 ml) was heated at 60° C. for 5 hours. Approximately half the solvent was evaporated off under reduced pressure and the residue cooled and carefully acidified with 1N hydrochloric acid. The pale yellow crystals which precipitated were separated by filtration, washed with water and air dried. Yield=1.27 g (76%). Recrystallization from ethanol-water (5:40) gave 2.03 g of white crystals; 0.86 g (51%). M.P. 182°–184° C.

Infrared (KBr, cm$^{-1}$): 3299 (m, s), 1771 (s), 1729 (s).

EXAMPLE 2

The following compounds were prepared according to the procedure of Example 1 from appropriate 2-methoxybenzaldehydes:

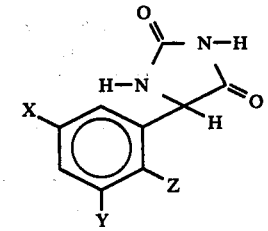

| Example | X | Y | Z | MP (°C.) | IR (cm$^{-1}$) (KBr) |
|---|---|---|---|---|---|
| 2 | F | Cl | OCH$_3$ | 199–201 | 1778, 1771 |
| 3 | Cl | CH$_3$ | OC$_2$H$_5$ | 173–5 | 1769, 1731 |
| 4 | F | Cl | OC$_2$H$_5$ | 181–4 | 1771, 1720 |

EXAMPLE 5

Repetition of the procedure of Example 1 but substituting equimolar amounts of the appropriate 2-alkyoxybenzaldehyde reactant for 5-chloro-2-methoxy-3-methylbenzaldehyde affords the following compounds:

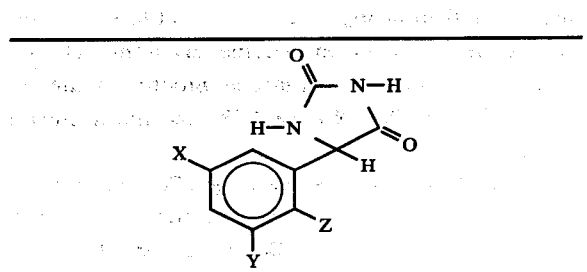

| X | Y | Z | X | Y | Z |
|---|---|---|---|---|---|
| —Cl | CH3 | O—n-C4H9 | —CH3 | F | OC2H5 |
| —F | Cl | O—n-C4H9 | —CH3 | CH3 | OCH3 |
| Cl | C2H5 | OCH3 | C2H5 | C2H5 | OCH3 |
| Cl | n-C4H9 | OCH3 | —CH3 | n-C4H9 | OCH3 |
| —F | CH3 | OCH3 | CH3 | n-C4H9 | O—n-C3H7 |
| —F | CH3 | O—n-C3H7 | —Cl | Cl | OCH3 |
| NO2 | CH3 | OCH3 | —Cl | F | OC2H5 |
| NO2 | Cl | OCH3 | —F | F | OCH3 |
| NO2 | F | OC2H5 | CH3 | CH3 | OCH3 |
| NO2 | Cl | O—n-C4H9 | CH3 | CH3 | OC2H5 |
| —CH3 | Cl | OCH3 | i-C3H7 | i-C3H7 | OCH3 |
| —C2H5 | Cl | OCH3 | i-C3H7 | i-C3H7 | O—n-C4H9 |

PREPARATION A

3-Chloro-5-Fluoro-3-Methoxybenzaldehyde

To a solution of sodium hydroxide (50 g, 1.25 mol) in water (70 ml) was added 2-chloro-4-fluorophenol (10 g, 0.068 mol) and chloroform (30 ml) and the mixture heated at reflux for two hours. An additional 30 ml of chloroform was added and refluxing continued for two more hours. This step was repeated once again after which the mixture was cooled to room temperature. The brown precipitate which formed was removed by filtration, then suspended in water and the suspension acidified with 3N HCl. The resulting tan solid, 3-chloro-5-fluoro-2-hydroxybenzaldehyde, was filtered, washed with water and dried; 4.03 g (34%). M.P. 81°–83° C.

The title compound was made by dissolving 3-chloro-5-fluoro-2-hydroxybenzalehyde (1.25 g, 7.2 mmol) in acetone (25 ml) and adding potassium carbonate (1.27 g, 9.2 mmol) and methyl iodide (1.3 g, 9.2 mmol). The mixture was stirred overnight at room temperature then filtered. The filter cake was washed with acetone and the combined filtrate and wash concentrated under reduced pressure to a gummy solid. The solid was partitioned between methylene chloride and water. The methylene chloride phase was separated, washed successively with water, 1N NaOH and brine, then dried (MgSO4) and concentration under reduced pressure. The pale yellow solid obtained (710 mg, 52% yield) melted at 59°–61° C.

The following compounds are similarly prepared from appropriate reactants:

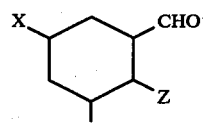

| X | Y | Z |
|---|---|---|
| F | Cl | O—n-C4H9 |
| F | CH3 | O—n-C3H7 |
| CH3 | CH3 | OCH3 |
| CH3 | n-C4H9 | OCH3 |
| Cl | Cl | OCH3 |
| Cl | F | OC2H5 |
| F | F | OCH3 |
| C2H5 | C2H5 | OCH3 |
| i-C3H7 | i-C3H7 | OCH3 |
| i-C3H7 | i-C3H7 | O—n-C4H9 |

PREPARATION B

5-Chloro-2-Methoxy-3-Methylbenzaldehyde

Titanium tetrachloride (24.3 g, 0.128 mole) is added to a solution of 4-chloro-2-methylanisole (10 g, 0.064 mol) in methylene chloride (150 ml) at 0° C. alpha,alpha-Dichloromethyl methyl ether (8.04 g, 0.070 mol) was then added dropwise with stirring over a three minute period at 0° C. The mixture was stirred for 30 minutes at 0° C. then poured into a saturated aqueous solution of sodium bicarbonate (700 ml). The organic layer was then separated and the aqueous phase extracted with methylene chloride. The combined organic extracts were washed with brine, dried (MgSO4) and concentrated in vacuo. The residue was chromatographed on a silica gel (300 g) column using hexane-ether (6-1) as eluent. Fractions of 15 ml each were collected. Fractions 21–50 were combined and evaporated in vacuo to a white solid (8.9 g). This solid was re-chromatographed on silica gel (300 g), eluting with hexane (15 ml fractions). Fractions 174–215 were combined and evaporated in vacuo to give 2.1 g of the title product as a white solid.

NMR: 2.3 (s, 3H), 3.9 (s, 3H), 7.4 (d, 1H), 7.6 (d, 1H), 10.4 (CHO).

The following compounds are similarly prepared from appropriate reactants:

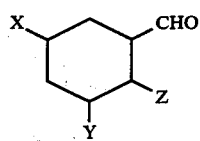

| X | Y | Z |
|---|---|---|
| Cl | CH3 | O—n-C4H9 |
| Cl | C2H5 | OCH3 |
| F | CH3 | OCH3 |
| CH3 | Cl | OCH3 |
| C2H5 | Cl | OCH3 |
| CH3 | F | OC2H5 |

I claim:

1. A method for treating a diabetic host for diabetes-associated complications which comprises administering to said host an effective amount of a compound having the formula

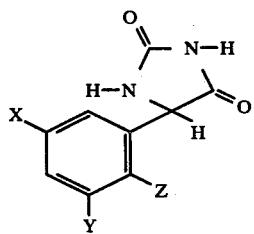

or a pharmaceutically acceptable salt thereof,
wherein each of X is fluoro, chloro, (C$_{1-4}$)alkyl or nitro;
Y is fluoro, chloro or (C$_{1-4}$)alkyl; and
Z is (C$_{1-4}$)alkoxy.

2. A method according to claim 1, wherein X is fluoro or chloro.

3. A method according to claim 2, wherein Y is chloro or methyl.

4. A method according to claim 3, wherein Z is methoxy or ethoxy.

5. The method according to claim 4, wherein X is chloro, Y is methyl and Z is methoxy.

6. The method according to claim 4, wherein X is chloro, Y is methyl and Z is ethoxy.

7. The method according to claim 4, wherein X is fluoro, Y is chloro and Z is ethoxy.

8. The method according to claim 4 wherein X is fluoro, Y is chloro and Z is methoxy.

* * * * *